United States Patent [19]

Miyazaki et al.

[11] Patent Number: 5,233,025
[45] Date of Patent: Aug. 3, 1993

[54] AMPHETAMINE PROTEIN COMPLEX AS IMMUNOGEN FOR OBTAINING ANTIBODIES SPECIFIC TO METHAMPHETAMINE

[75] Inventors: Jinsei Miyazaki, Higashiosaka; Makoto Taketani, Ashiya; Tadayasu Mitsumata, Hirakata, all of Japan

[73] Assignee: Matsushita Electric Industrial Co., Ltd., Osaka, Japan

[21] Appl. No.: 651,809

[22] Filed: Feb. 7, 1991

Related U.S. Application Data

[62] Division of Ser. No. 401,247, Aug. 31, 1989, Pat. No. 5,026,827.

[30] Foreign Application Priority Data

Sep. 2, 1988 [JP] Japan .................. 63-220931

[51] Int. Cl.$^5$ .......................... C07K 15/28; C12N 5/12
[52] U.S. Cl. ........................ 530/388.9; 530/387.1; 530/388.1; 530/405; 435/70.21; 435/172.2; 435/240.27; 424/88
[58] Field of Search ............... 530/388.1, 389.1, 388.9, 530/389.8, 387.1, 405; 435/240.27, 70.21, 172.2; 514/654; 424/88

[56] References Cited

U.S. PATENT DOCUMENTS 3,878,187 4/1975 Schneider et al. .................. 530/363
3,996,344 12/1976 Gross ............................... 424/1.5

FOREIGN PATENT DOCUMENTS 0311383 10/1988 European Pat. Off. .

OTHER PUBLICATIONS

Tokura et al. Analytical Biochem 161:117-122 (1987).
Usagawa et al. J. Immunol. Methods 119:111-115 (1989).
Yoshii et al. Nippon Hoigaku Zassih 41:342-346 (1987)
Yoshii et al. N. Alkyl Effects of Methamphetamine Analogues on the Reactivity to Anti-Ma Antibody English Translation.
Oi et al. in Selected Methods in Cellular Immunology: ed. Mishell Chapter 17 pp. 351-372 (1980).
Inayama et al, Biological Abstracts, vol. 71, No. 7, 1981, Abstract No. 48539.
Grinstead, Clinical Chemistry, vol. 35, No. 9, Sep. 1989, pp. 1998-1999.
Badcock et al, Clinical Chemistry, vol. 33, No. 6, 1987, p. 1080.
Cheng et al (1973), FEBS Lett 36(3):339-342.
Chem Abstract 108(15):126018d, Yoshii et al (1987); Nippon.
Hoigaku Zasshi 41(4):342-346 (and English Translation).
Usagawa et al (1989), J. Immunol. Methods 119:111-115.

Primary Examiner—David L. Lacey
Assistant Examiner—Phillip Gambel
Attorney, Agent, or Firm—Stevens, Davis, Miller & Mosher

[57] ABSTRACT

A N-(4-aminobutyl)amphetamine-protein complex has been synthesized to be used as an immunogen to prepare an antibody having a higher affinity to methamphetamine that to the hapten N-(4-aminobutyl)amphetamine. The antibody prepared by the use of the complex has 1,000 times the affinity to methamphetamine as that of an antibody prepeared by the use of N-(4-aminobutyl)methamphetamine-protein complex as an immunogen.

2 Claims, 3 Drawing Sheets

(MA)

(ABMA)

(ABAP)

(AP)

AMPHETAMINE PROTEIN COMPLEX AS IMMUNOGEN FOR OBTAINING ANTIBODIES SPECIFIC TO METHAMPHETAMINE

This is a division of U.S. application Ser. No. 401,247 filed Aug. 31, 1989, now U.S. Pat. No. 5,026,827.

BACKGROUND OF THE INVENTION

1. Field of the Invention

The present invention relates to a method for producing a highly efficient antibody which takes the most important role in immunoassay useful in the fields of medical diagnosis, chemical analysis, etc., and more particularly, to a method for producing an antibody having a high affinity to a low molecular weight compound; namely, a hapten which is per se incapable of causing an immunoresponse.

In more detail, the present invention relates to the production of an antibody or monoclonal antibody having a high affinity to methamphetamine which exerts on a central excitatory action and is an analeptic.

2. Related Art Statement

In detecting a trace component in blood or a specific component in the atmosphere, it is necessary to detect with certainty a specific component present in a trace amount from very many impurities. In recent years, immunoassay based on the reaction of an antibody with an antigen has been extensively investigated for this purpose.

Immunoassay is roughly classified into radioimmunoassay using a radioactive isotope and enzyme-immunoassay (EIA) using an enzyme. From the viewpoints of safety and simplicity, EIA is more advantageous.

Enzyme-linked immunosorbent assay (ELISA) which is typical EIA is described below by referring to FIG. 1. In FIG. 1, numeral 1 denotes a microplate made of plastic such as polystyrene which non-specifically adsorbs protein. Numeral 2 denotes a solid phase antigen adsorbed onto microplate 1, which antigen is prepared by introducing a suitable functional group into an antigen as analyte and chemically binding the antigen to protein via the functional group. Numeral 3 is an antibody capable of binding to the analyte and the antibody binds to solid phase antigen 2 in an equilibrated state. That is, antibody 3 is immobilized to microplate 1 via solid phase antigen 2. When an antigen 4 as analyte is introduced into the system, solid phase antigen 2 and antigen 4 as analyte competitively bind to antibody 3. Therefore, a part of antibody 3 binds to antigen 4 as analyte and as the consequence, a part of antibody 3 remains unbound to microplate 1. As a matter of course, the larger the quantity of antigen 4 as analyte, the greater the quantity of antibody 3 that remains unbound to microplate 1. At this stage, the unbound antibody 3 can be removed by washing. After removing the unbound antibody 3, antibody 5 which is capable of binding to antibody 3 is added to the system. Antibody 5 can be any antibody that is chemically bound to enzyme 6 in a definite proportion. After antibody 5 unbound to antibody 3 is removed by washing, the activity of enzyme 6 is determined. There is a positive correlation between the activity and the quantity of enzyme 6 so that the quantity of enzyme 6 can be quantitatively determined by assaying the reactivity. When the quantity of enzyme 6 is known, it is possible to quantitatively determine the quantity of antibody 3 bound to microplate 1 via the solid phase antigen 2 and then quantitatively determine the quantity of; antigen 4 as analyte. In this case, a primary factor to determine the detection sensitivity is an affinity of antibody 3 to antigen 4 as analyte.

An antibody is one of the protein produced by an; organism which has the property of selectively binding only to a specific substance, i.e., antigen. An antigen is roughly classified into two types due to differences in the production of an antibody binding to the antigen. One is an antigen that can induce the production of an antibody by injecting the antigen directly into animal. In general, macromolecular substances having a molecular weight of several tens of thousands or more correspond to such an antigen. Another type of antigen has a relatively small molecular weight and, by chemically bonding to a suitable protein, it can acts as an immunogen, inducing the production of an antibody for the first time. In particular, the latter antigen is called hapten. A method for producing an antibody to hapten as antigen is described in Hapten and Carriers, O. Makela and I. J. T. Seppala, Handbook of Experimental Immunology, 4th edition, Volume 1, Chapter 3, edited by D. M. Weir, Blackwell Scientific Publications, Oxford, 1986. That is, it is described that where hapten contains a functional group capable of chemical binding, hapten is bound to protein via the functional group to form an immunogen. If any functional group is absent in the hapten, an immunogen is generally obtained by introducing an appropriate functional group such as an amino group, a carboxyl group and a hydroxyl group and a spacer composed of an alkyl group having 1 to about 10 carbon atoms into the hapten to synthesize hapten derivatives and binding the derivatives to a suitable protein using a crosslinking agent. More specifically, Takami et al. report the production of antibody using as a hapten methamphetamine (MA) having a central excitatory action which is an analeptic [Takami, Fukuda and Takahashi, Japan, J. Legal Med., 37 (4), 417, 1983]. It is reported that an aminobutyl group is introduced to the secondary amino group of MA to produce aminobutyl methamphetamine (ABMA). The derivative is bound to protein and the obtained product is used as an immunogen.

However, the present inventors' study has revealed that the antibody produced using the immunogen has a higher affinity to the antigen derivative, i.e., ABMA, rather than to the desired antigen, i.e., MA. That is, the antibodies produced by the prior art methods are antibodies not to the antigen but to the antigen derivatives. The antigen derivatives have a structure different from that of the antigen, because functional groups, spacers, etc. are introduced. Thus, there is clearly revealed a problem that an antibody having a high affinity to the desired antigen is produced only with difficulty. As the result, upon assaying an antigen as analyte according to, for example, FLISA described above, using the antibody produced by the prior art methods, even though the antigen an analyte is introduced into the system in large quantities, the quantity of unbound antibody does not increase, so that it is impossible to detect the antigen as analyte with high sensitivity.

SUMMARY OF THE INVENTION

An object of the present invention is to produce an antibody having a high affinity to the desired antigen, as compared to the antibody produced using a conventional immunogen which is prepared by chemically binding antigen derivative to a protein.

According to the present invention, a substance having a high similarity in chemical structure to the desired antigen under conditions such that functional groups and spacers are introduced thereinto is chosen as a starting material. Into the starting material are introduced a functional group and spacer to obtain an antigen derivative. The thus obtained derivative is bound to protein via the functional group to produce an immunogen. By using the thus produced immunogen, an antibody having a high affinity to the desired antigen is obtained since the immunogen carries a chemical structure highly similar to that of the desired antigen.

Accordingly, it is the main object of the present invention to provide an immunogen using such an antigen derivative, an antibody produced by the immunogen, hybridoma cells obtained by cell fusion of spleen cells sensitized with the immunogen and myeloma cells, and a monoclonal antibody produced from the hybridoma.

In more detail, it is the object of the present invention to provide an immunogen obtained by introducing a spacer and a functional group capable of binding to a protein at the site of the hydrogen atom of a starting material, which corresponds to a substance wherein the alkyl group of the desired antigen molecule is substituted with a hydrogen atom, and binding the thus prepared antigen derivative to protein via the functional group. The immunogen of the present invention is one having a highly similar chemical structure to that of the desired antigen, as compared to conventional immunogens produced by using the desired antigen as a starting material, introducing a functional group and spacer into the starting material and binding to protein via the fructional group. As the result, the antibody having a high affinity to the desired antigen can be produced.

DETAILED DESCRIPTION OF THE INVENTION

Figure 1:
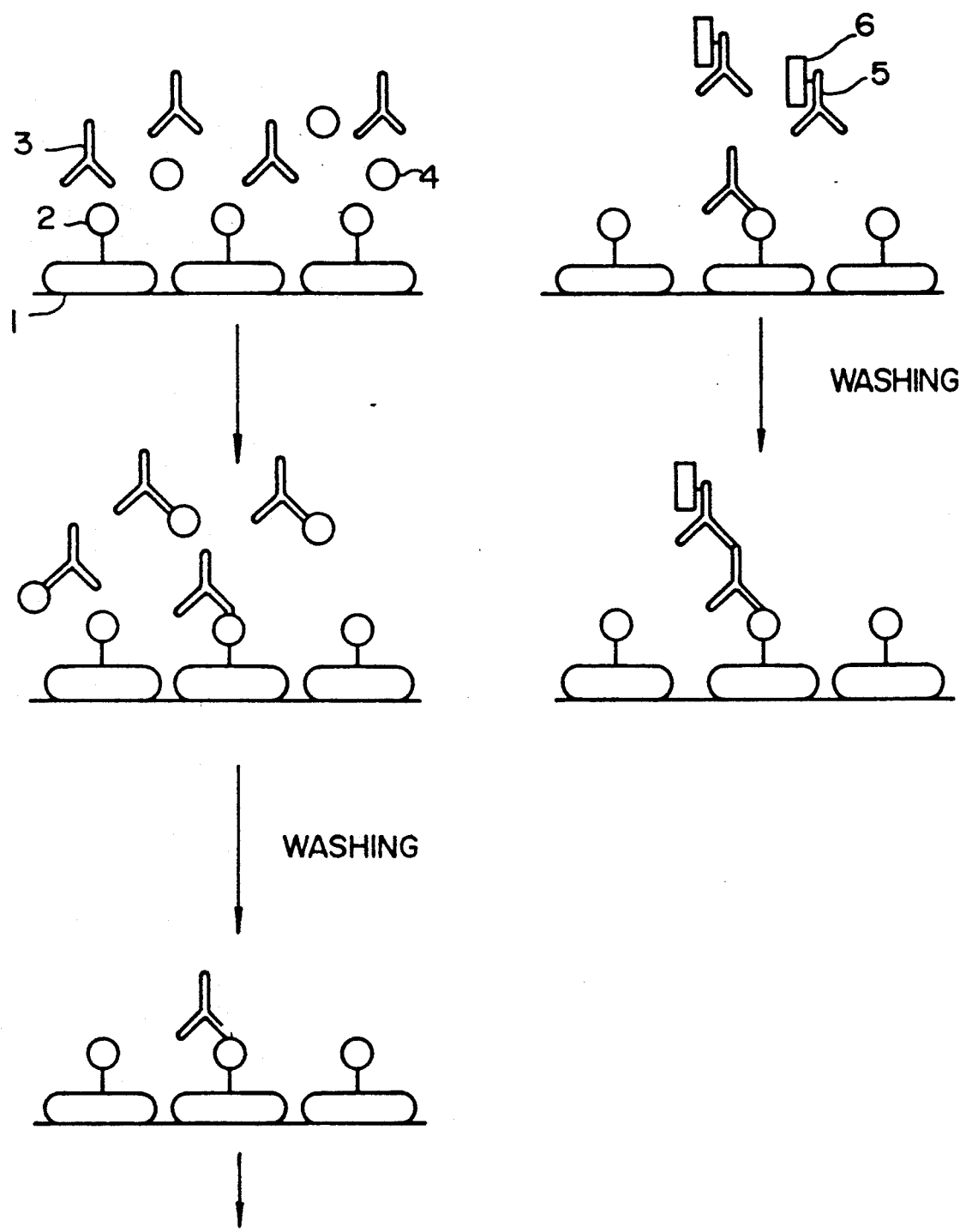
FIG. 1 shows an illustrative outline of ELISA, wherein numeral 1 denotes a microplate, numeral 2 denotes a solid phase antigen which is prepared by introducing a suitable functional group into an antigen as analyte and chemically binding the antigen to protein via the functional group, numeral 3 denotes an antibody capable of binding to the antigen as analyte, numeral 4 denotes an antigen as analyte, numeral 5 denotes an antibody capable of binding to antibody 3, and numeral 6 denotes enzyme chemically bound to antibody 5.
Figure 2:
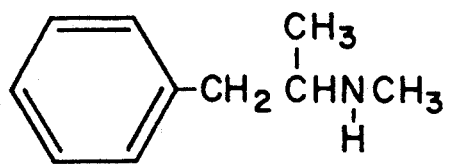
FIG. 2 shows a chemical structure of methamphetamine (MA).
Figure 3:
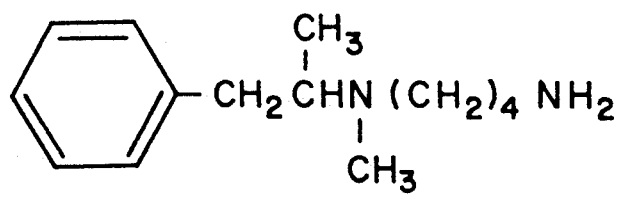
FIG. 3 shows a chemical structure of aminobutyl methamphetamine (ABMA).
Figure 4:
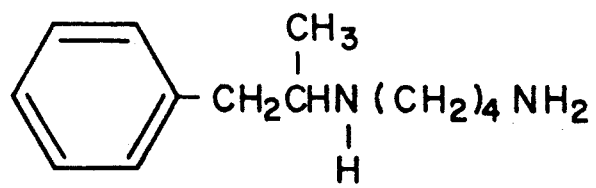
FIG. 4 shows a chemical structure of aminobutyl amphetamine (ABAP).
Figure 5:
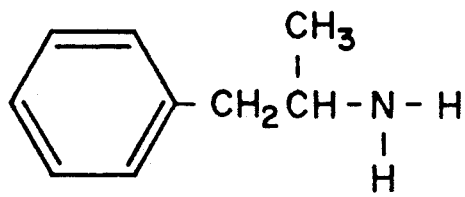
FIG. 5 shows a chemical structure of amphetamine (AP).

As an embodiment of the present invention, there is described below the production of an antibody having a high affinity to the desired antigen, using as the desired antigen methamphetamine (MA) having a central excitatory action, which is an analeptic. In this embodiment, an antigen derivative (aminobutyl amphetamine, ABAP) was obtained by introducing an aminobutyl group as the functional group capable of binding with protein into amphetamine (AP) (cf. FIG. 5), which corresponds to a compound wherein methyl as the N-alkyl group in MA is substituted with hydrogen atom. Structures of MA, ABMA, AMAP and AP are shown in FIGS. 2, 3, 4 and 5, respectively. High similarity in chemical structure is noted between MA and ABAP.

Another preferred examples of the antigen derivative include amphetamine derivatives represented by the following general formula:

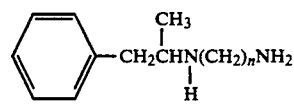

wherein n represents an integer. n is preferably an integer of 1 to 10. When n is 4, the structural formula described above represents ABAP.

These amphetamine derivatives can readily be obtained by reacting AP with, for example, an N-haloalkylphthalimide such as N-bromotbutylphthalimide and then treating with hydrazine.

Next, ABAP is bound to keyhole limpet hemocyanin (KLH) via an aminobutyl group to form an immunogen. Alternatively, proteins such as gamma globulins derived from chicken, etc. and bovine serum albumin may also be used. Other amphetamine derivatives may also be bound to protein such as KLH through the aminoalkyl group in the molecule thereof. Binding between the amphetamine derivatives such as ABAP and protein can be effected in a conventional manner. That is, the binding can be performed using ordinary binding reagents such as N-succinimidyl-3-(2-pyridyldithio)propionate (SPDP), tolylene-2,4-diisocyanate, glutaraldehyde, periodic acid, 1,5-difluoro-2,4-dinitrobenzene (DFDNB), succinimidyl 4-(N-maleimidomethyl)cyclohexane-1-carboxylate (SMCC), N-(γ-maleimidobutyryloxy)succinimide (GMBS) and N-(ε-male-imidocaproyloxy)succinimide (EMCS).

By injecting the thus obtained immunogen into animal, an antibody having a high affinity to MA, namely, anti-MA antibody is produced in animal sera. Thus, collection of sera from animal sensitized with the immunogen gives an antibody having a high affinity to MA. The thus obtained sera used without further purification as an agent for immunoassay, i.e., ELISA. Any animal can be used for immunization so long as it is mammalian. For simplicity of experiment, mice were chosen in an embodiment of the present invention. A/J strain mice are advantageous since the strain causes the highest immune response.

By fusing the spleen cells collected from an animal sensitized with the aforesaid immunogen with myeloma cells, hybridoma cells which can produce a monoclonal antibody having a high affinity to MA can be obtained. The hybridoma cells can be produced by the method known as the Kohler and Milstein method [Kohler et al., Nature, 256, 495 (1975)]. For example, the hybridoma cells can be harvested by using X63-Ag8.653, which is one of 8-azaguanine-resistant strains, as mouse myeloma cells, fusing the cells with spleen cells in the presence of a fusion accelerator such as polyethylene glycol and Sendai virus, culturing the resulting fused cells in HAT medium and collecting the hybridoma which produces antibody having a high affinity to MA.

The hybridoma is cultured in a suitable medium and a monoclonal antibody having a high affinity to MA can be collected from the supernatant.

Using the antibody and monoclonal antibody having a high affinity to MA which can be obtained by the present invention, MA in blood can be quantitatively determined with high sensitivity, for example, by ELISA. Accordingly, these antibodies are extremely useful in the field of diagnosis, chemical analysis, etc.

Hereafter the present invention is described according to the procedure in more detail, by referring to the examples below.

EXAMPLE 1

Firstly, a process for producing antisera is described below.

(1) Synthesis of ABAP

A mixture of 2.00 g of amphetamine (AP), 4.17 g of N-bromobutylphthalimide (manufactured by Aldrich Chemical Company Inc.) and 3.14 g of sodium hydrogen-carbonate was refluxed in 10 ml of benzene for 16 hours. After the solvent was removed from the reaction solution, the residue was purified by preparative thin layer chromatography (TLC, manufactured by Merck and Co. Inc.) using silica gel as the carrier. As an elution solvent, a mixture of methanol and chloroform in a volume ratio of 5:95 which had been previously saturated with ammonia was used the Rf value of the product was 0.7. Extraction of the product on silica gel with methanol gave 1.59 g of N-(4-phthalimidylbutyl)amphetamine (PIBAP).

In 5 ml of 95% ethanol was dissolved 1.50 g of PIBAP and, 0.25 g of hydrazine monohydrate was added to the solution. The mixture was refluxed for 1.5 hours to form a small amount of white precipitates. After the mixture was again filtered, the filtrate was rendered acidic with 1N hydrochloric acid and the formed white precipitates were removed. The solution was further rendered alkaline with sodium hydroxide, whereby the oily phase was separated. The oily phase was extracted with diethyl ether. After removing the solvent by distillation, the residue was purified by TLC under the same conditions described above. The product was reacted with ninhydrin to form a bluish purple color. Utilizing the reaction, the product on TLC was confirmed and 0.75 g of N-(4-aminobutyl)amphetamine (APAP) was finally obtained.

(2) Preparation of immunogen

In 200 μl of 0.5N hydrochloric acid was dissolved 19.1 mg of ABAP. The solution was diluted with 4.8 ml of 0.1M phosphate buffer solution (pH 7.5). A solution of 12.5 mg of thiol group-introducing N-succinimidyl-3-(2-pyridyldithio)propionate (SPDP, manufactured by Pharmacia LKB Biotechnology) in 1 ml of ethanol was added to the solution followed by reacting for 30 minutes with stirring. In order to verify the progress of the reaction, the reaction solution was developed on TLC. As the elution solvent, the same solvent mixture as described above was used. SPDP is confirmed by TLC as a black spot that absorbs UV light at 245 nm. In the reaction solution after stirring for 30 minutes, the black spot on TLC disappeared, indicating that SPDP fully reacted with ABAP. Thus, the conjugate of SPDP and ABAP (AP-SPDP) was obtained.

On the other hand, KLH was dissolved in 0.1M phosphate buffer (pH 7.0) containing 0.1M NaCl to prepare 2.2 mg/ml of KLH solution. A solution of 51.6 mg of SPDP in 4.2 ml of ethanol was dropwise added to the KLH solution and the mixture was reacted for 12 hours with stirring. Thereafter, unreacted SPDP in the reaction solution was separated by gel filtration using Sephadex G-25 (manufactured by Pharmacia LKB Biotechnology) to give the conjugate of KLH and SPDP (KLH-SPDP). Sephadex G-25 was packed in a column having a diameter of 4 cm and a length of 50 cm and used at a flow rate of 6.9 ml/min. Dithiothreitol (DTT) was dissolved in 0.1M phosphate buffer and 1.8 ml of the resulting solution was added to KLH-SPDP to perform reduction. After the mixed solution was again subjected to gel filtration under the same conditions as described above using Sephadex G-25 column, the AP-SPDP solution was gradually added to 106 ml of the solution. After thirty minutes after, gel filtration was carried out under the same conditions as described above using Sephadex G-25 column, whereby 14.3 molecules of AP was introduced per 1 mol of KLH. The thus obtained conjugate of KLH and AP (AP-KLH) was used as an immunogen.

(3) Method for immunization

The AP-KLH solution was diluted with 0.1M phosphate buffer (pH 7.0) to adjust the concentration of KLH to 1 mg/ml. The AP-KLH solution was mixed with complete Freund's adjuvant in an equivalent amount and the mixture was emulsified with a homogenizer. The emulsion was intraperitoneally injected to 8 week old mice. A dose of the injection was 100 μl per mouse. The strain of mice used was A/J as described above.

(4) Evaluation of antisera by ELISA 18 weeks after immunization with AP-KLH, sera of mice were collected. Using the sera, ELISA was performed and detection sensitivity was determined when using MA and ABMA as analytes. ELISA was performed under the following conditions.

Figure 6:
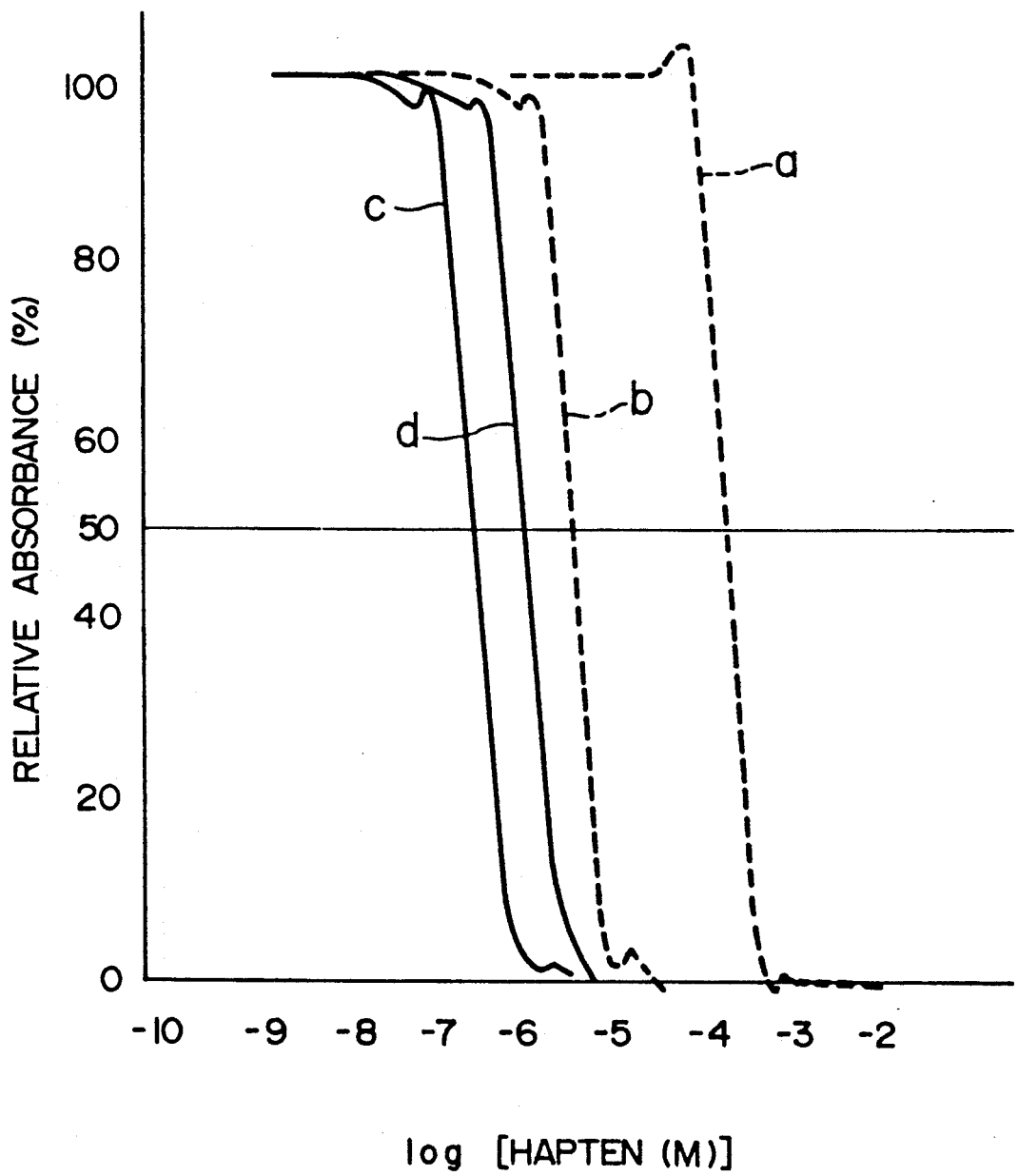
FIG. 6 is a graph comparing the detection sensitivity of MA with that of ABMA in ELISA with antisera obtained by the prior art and the process of the present invention, wherein the abscissa indicates logarithms of concentrations of MA and ABMA added and the ordinate indicates enzyme activity in terms of relative absorbance. Where a relative absorbance decreases in a certain concentration of MA, MA of that concentration can be detected. The dotted line horizontally drawn represents 50% relative absorbance. Curves a, b, c and d represent a curve for detecting MA using an antibody produced by the prior art method, a curve for detecting ABMA using the antibody produced by the prior art method, a curve for detecting MA using an antibody produced by the process of the present invention and a curve for detecting ABMA using an antibody produced by the process of the present invention, respectively.

A chemically bound conjugate of BSA and ABMA (MA-BSA) wherein 0.4 molecule of ABMA as the antigen derivative had been introduced into 1 molecule of bovine serum albumin (BSA) was used as a solid phase antigen. MA-BSA was adsorbed and immobilized onto a 96 well polystyreneplate for ELISA (manufactured by Coaster Corporation). The antisera collected from mice were diluted with phosphate buffered saline (PBS) to 10,000-fold and the diluted antisera were mixed in 1:1 with MA or ABMA solutions having various concentrations. The solution mixture was separately charged in each well of the 96 well plate for ELISA by 100 μl each. After three hours, the solution mixture was removed and the 96 well plate for ELISA was washed with PBS. By this operation, the antibody in the antisera unbound to MA-BSA on the plate was removed. Then, the antibody capable of binding to the mouse antibody contained in the antisera was separately charged in the same amount as described above. The antibody is a so-called POD-labeled antibody, which is an antibody chemically bound to peroxidase (POD). After thirty minutes, the POD-labeled antibody solution was removed and the 96 well plate for ELISA was washed again with PBS. By this procedure, the POD-labeled antibody which was unbound to the mouse antibody whichever attached to the solid phase antigen on the plate was removed. On the other hand, 40 mg of o-phenylenediamine (OPD) was dissolved in 10 ml of phosphate citrate buffer (pH 5.0) and 4 µl of 30% $H_2O_2$ was mixed with the solution. The solution mixture was separately charged in the 96 well plate for ELISA, in 100 µl per well, which had been washed with PBS after the removal of the unbound POD-labeled antibody. After one to two minutes, OPD was oxidized by the action of POD of the POD-labeled antibody bound to the plate, whereby the formation of a color having the maximum absorption at 492 nm was observed. After the enzyme reaction was terminated by separately charging 25 µl each of 4N sulfuric acid in each well, the absorbance of the solution in each well was determined at 492 nm by means of a spectrophotometer. The results are shown by solid lines in FIG. 6. For the purpose of comparison, with respect to the sera collected from mice 18 weeks after the immunization, the mice being sensitized with the chemically bound conjugate (MA-KLH) of ABMA and KLH synthesized in a manner similar to the AP-KLH conjugate described above, ELISA was performed under the same conditions as described above. The results are shown by dotted lines in FIG. 6. In FIG. 6, the ordinate represents a relative absorbance at 492 nm and indicates the relative amount of mouse antibody in the antisera bound to the solid phase antigen. The abscissa represents a concentration of MA or ABMA in the solution mixture of the antisera used for the assay with MA or ABMA.

The results shown in FIG. 6 are examined below. Turning firstly to the antisera obtained by immunizing with MA-KLH, the MA concentration showing 50% reduction in relative absorbance was found to be $10^{-3.6}$M from Curve a. With respect to ABMA, the relative absorbance decreased to 50% at the concentration of $10^{-5.2}$M based on Curve b. That is, it is concluded that ABMA inhibits the binding of the mouse antibody in the antisera to the solid phase antigen by approximately 50 times stronger than MA. In other words, the antibody obtained by immunization with MA-KLH binds to ABMA more strongly by about 50 times, rather than to MA. On the other hand, taking into account the facts that the solid phase antigen used for ELISA is the chemically bound conjugate of ABMA and BSA and contains the same structure as that of ABMA, it is expected that the antibody obtained by immunization with MA-KLH would bind to the solid phase antigen more strongly than to MA. As described above, the solid phase antigen and the antigen as analyte competitively bind to the antibody; as the result, the antibody is inhibited to bind to the solid phase antigen so that the amount of the antibody bound to the solid phase antigen decreases. This phenomenon is utilized for ELISA. Where the antibody binds to the solid phase antigen more strongly, it is difficult to cause inhibition on the binding of the antibody to the solid phase antigen by the antigen as analyte, resulting in reduction of measurement sensitivity.

On the other hand, in the antisera immunized with AP-KLH, the MA concentration showing 50% reduction in relative absorbance was found to be $10^{-6.5}$M from Curve c and the ABMA concentration was found to be $10^{-5.6}$M from Curve d. That is, the antibody obtained by immunization with AP-KLH binds to MA more strongly by about 50 times than to ABMA, conversely where the antibody was obtained by immunization with MA-KLH. Accordingly, there is no chance of causing reduction in measurement sensitivity as described above. In fact, according to ELISA using the antisera obtained by immunization with AP-KLH, the MA concentration, $10^{-6.5}$M, at which relative absorbance decreased to 50% was as low as approximately 1/1000, when compared to the case of using the antisera obtained by immunization with MA-KLH.

The immunogen based on the concept described above is also generally applicable to the production of an antibody to a hapten having a molecular weight below 1000, with respect to other than MA mentioned in this example. In addition, antibody produced from hybridoma cells obtained by fusing spleen cells collected from the animal sensitized in this example with myeloma cells, so-called monoclonal antibody, can also exert the same properties as the antisera as a matter of course. That is, a monoclonal antibody can be obtained which has a much high affinity to a hapten as antigen. Hereafter a process for producing the monoclonal antibody is described below.

EXAMPLE 2

Using the mice in which production of the antibody showing a high affinity to MA rather than ABMA was confirmed in Example 1, a monoclonal antibody was produced. Hereafter the process is sequentially described.

(1) Boost of mouse

At the point of 7 weeks after the immunization with AP-KLH, the mice were subjected to a booster treatment to cause hypertrophy of the spleen. That is, AP-KLH was diluted to 1 mg/ml and 100 µl of the dilution was intraperitoneally injected to each mouse.

(2) Cell fusion

Three days after the booster, spleen cells were taken out of the mice and fused with mouse myeloma cells X63-A8.653. The procedure is shown below in detail.

(i) After the mice were sacrificed and pasteurized, the mice were moved to a clean bench. The following procedure was all aseptically performed in the clean bench.

(ii) The spleen was withdrawn from each mouse and transferred onto a stainless mesh which had been previously immersed in Iscove's modified Dulbecco's medium (IMDM, manufactured by Sigma Chemical Company). The spleen was cut with scissors to form about 10 stabs and carefully squeezed using a glass rod for withdrawing cells. By this operation, the spleen cells were suspended in IMDM. After 5 ml of IMDM suspended with the spleen cells was transferred to a centrifuging tube, the cells remained on the mesh was further washed with 5 ml of IMDM. The washed cells were also charged in the centrifuging tube. In the subsequent procedures up to (ix), the centrifuging machine was cooled and ice bath was used on occasion so as to keep the temperature of cells at 4° C. as best as possible.

(iii) The suspension of spleen cells was centrifuged at 800 g for 7 minutes and the supernatant was removed by an aspirator.

(iv) In order to destroy red blood cells which are unnecessary components, 10 ml of Tris buffer containing $NH_4Cl$ was added and the cells adhered to the bottom were agitated with a pipette to loosen them. After allowing to stand on ice for 5 to 10 minutes, centrifugation was performed at 800 g for 7 minutes and the supernatant was removed by an aspirator.

(v) Hanks' Balanced Salt Solution (manufactured by Research Institute for Microbial Disease, Osaka University), 10 ml, was added to the system and the cells remained at the bottom of the centrifuging tube were agitated to loosen them and allowed to stand on ice for 5 to 10 minutes. where the tissue fragments precipitated, the cell suspension alone was transferred to another centrifuging tube so as not to scoop the fragments. The cell suspension was centrifuged at 800 g for 7 minutes and the supernatant was removed by an aspirator.

(vi) Again 10 ml of Hanks' Balanced Salt Solution was added and the cells at the bottom of the tube were agitated to loosen them. Centrifugation was carried out at 800 g for 7 minutes and the supernatant was removed by an aspirator.

(vii) Hanks' Balanced Salt Solution, 13 to 14 ml, was added and the cells at the bottom of the tube were agitated to loosen them.

(viii) To 50 $\mu$l of the spleen cell suspension obtained in (vii) was added 50 $\mu$l of Nigrosine solution which was a cell staining solution. About 1 minute after, a cell count was determined with a hemocytometer. The cell count was $5.1 \times 10^6$ cells/ml.

(ix) (The following operation is preferably conducted alternatively, utilizing the centrifuging time from the preceding (vi), thereby to count the spleen cells and myeloma cells at the same time. Further in the following operation, centrifuging machines having different temperatures are used so as to avoid cooling myeloma cells to below normal temperature.) Myeloma cells, 45 ml, during the course of culture was transferred to 50 ml of a centrifuging tube followed by centrifugation at 800 g for 7 minutes. The supernatant was withdrawn by an aspirator.

(x) Hanks' Balanced Salt Solution, 10 ml, was added and the myeloma cells at the bottom of the tube were agitated to loosen them. Centrifugation was carried out at 800 g for 7 minutes and the supernatant was removed by an aspirator. This procedure was repeated twice.

(xi) After 13 ml of Hanks' Balanced Salt Solution was added, the myeloma cells at the bottom of the tube were agitated to loosen them.

(xii) The cells were counted in a manner similar to (viii). The cell count was $1.5 \times 10^6$ cells/ml.

(xiii) Nine milliliters of the spleen cell suspension obtained in (viii), which had been reverted to normal temperature, was well mixed with 6 ml of the myeloma cell suspension obtained in (xii). After centrifuging at 2000 g for 5 minutes, the supernatant was removed by an aspirator.

(xiv) (The following operation was performed on a water bath at about 40° C. put in the clean bench). While gently agitating, 0.5 ml of polyethylene glycol (PEG) having a mean molecular weight of 1500 was added to the precipitated cells obtained in (xiii) over one minute. Agitation was continued for further 1.5 minutes.

(xv) After 5 ml of IMDM was further added at a rate of 1 ml/min, 5 ml of IMDM was added over one minute subsequent thereto. After 10 ml of IMDM was finally added, centrifugation was performed at 1000 g for 7 minutes and the supernatant containing PEG was completely removed by an aspirator.

(xvi) To the precipitated cells obtained in (xvi) was added 3 ml of the spleen cell suspension of (viii) as feeder cells and HAT medium (manufactured by Sigma Chemical Company) containing 10% fetal cow serum (FCS) was further added to make the whole volume 23 ml. After the cells were loosened with a pipette, 100 $\mu$l each was separately charged in each well of a 96 well plate for incubation. The foregoing operation was performed using two mice and the cell suspension was individually charged in 6 plates in total.

(xvii) The plates were transferred in a $CO_2$ incubator and the incubation was initiated. The $CO_2$ concentration and temperature in the incubator were set to 5% and at 37° C.

(xviii) One day after, 100 $\mu$l each of HAT medium was added per each well. The incubation was continued for a week.

(3) Production of monoclonal antibody

With respect to the plate that passed one week after the initiation of culture of the hybridoma cells in HAT medium, the following operation was conducted.

(i) From each well, 100 $\mu$l of the culture supernatant was taken and diluted with PBS to prepare 2 to 10,000-fold serial dilution. Using the serial dilution, ELISA was performed. As a solid phase antigen, conjugate (MA-BSA), in which 0.4 molecule of MA was chemically bound to BSA per 1 molecule of BSA, was used but no analyte was added. Other conditions were identical with those for ELISA described above. According to such ELISA, binding abilities of the antibodies in the respective culture supernatants to the solid phase antigen can be compared with each other. That is, in the culture supernatant showing a high absorbance in a large dilution degree, there is a high possibility that an antibody having a high affinity to the solid phase antigen is contained. Several culture supernatants were chosen from those having a high absorbance and incubation was continued only with the cells in the wells from which these culture supernatants were harvested. A culturing scale was set to appropriately grow bigger.

(ii) With respect to the culture supernatants chosen in (i), ELISA was performed more strictly. The culture supernatants were appropriately diluted and MA-BSA was used as the solid phase antigen. MA was added as analyte. Other conditions were identical with those for ELISA described above. Nineteen culture supernatants were chosen from those showing a high sensitivity in measurement of MA and incubation was continued only with the cells in the wells from which these culture supernatants were harvested.

(iii) The cells that produced the 19 culture supernatants chosen were suspended in IMDM medium, respectively and the cells were counted using Nigrosine.

(iv) Each cell suspension was diluted with HT medium (manufactured by Sigma Chemical Company) to adjust so as to contain one cell per 100 $\mu$l.

(v) The thymus was withdrawn from mouse of 5 weeks after birth. The thymus cells were suspended in HT medium to adjust so as to contain $2 \times 10^5$ thymus cells per 100 $\mu$l.

(vi) The thymus cell suspension of (v) was individually charged by 100 μl per each well in 10 plates of 96 well plate for incubation. Furthermore, the cell suspension of (iv) was added by 100 μl each per well.

(vii) While continuing the incubation in a $CO_2$ incubator, the culture supernatants were subjected to ELISA. The conditions were the same as in (ii). Regarding the cells from which the sensitivities showing a high sensitivity for measurement of MA, the incubation was continued while gradually growing an incubation size suitably. As the result of continuous selection by ELISA, 5 wells were finally selected. That is, 5 monoclonal antibody-producing cell lines were obtained. These cells were continuously cultured in 200 ml of IMDM medium until $5 \times 10^5$ cells were contained per 1 ml.

Among the 5 cell lines, a cell line 2D55A producing a monoclonal antibody having a highest affinity to MA has been deposited into Fermentation Research Institute Agency of Industrial Science and Technology (FRI, Ibaraki-ken, JAPAN) under the Budapest Treaty and has been given Acession No. FERM BP-2564.

(4) Storage of cells

Each culture liquid from the finally selected cell lines was transferred to a centrifuging tube. After centrifuging at 800 g for 7 minutes, the culture supernatant was removed by an aspirator. The cells at the bottom was suspended in a solution of FCS in dimethylsulfoxide (DMSO) in 9:1. The suspension was adjusted tó contain $5 \times 10^6$ cells per 1 ml. After freezing the suspension at $-80°$ C., the frozen suspension was transferred into the liquid nitrogen, which was made in a stored state over a long period of time.

(5) Purification of antibody

By affinity chromatography using Protein A-Sepharose 4B (manufactured by Pharmacia LKB Biotechnology), monoclonal antibody was purified from the culture supernatant of the cells. It was confirmed by SDS polyacrylamide gel electrophoresis that the purified monoclonal antibody was IgG composed of H chain having a molecular weight of about 50,000 and L chain having a molecular weight of about 20,000.

(6) Comparison of antibody affinity to various haptens

Among the purified monoclonal antibody, ELISA was applied to monoclonal antibody produced by cell line 2D55A. As the solid phase antigen, MA-BSA was used and assay was performed with respect to 4 haptens of MA, ABMA, AP and ABAP. Other conditions for the assay were the same as those in ELISA described above. These haptens were compared in terms of the concentration required for 50% reduction in relative absorbance at 492 nm. AP showed the highest concentration and the concentration was then reduced in the order of ABMA, ABAP and MA. AP required the concentration by about 100 times that of MA in order to cause 50% reduction in relative absorbance at 492 nm. That is, it was established that by using AP-KLH as the immunogen, the antibody having the highest affinity to MA out of the 4 haptens described above could be produced.

What is claimed is:

1. A hybridoma cell line having the accession number of FERM BP-2564.

2. A monoclonal antibody produced by the hybridoma cell line having the accession number of FERM BP-2564 wherein said antibody was generated by immunization with an immunogen consisting of the hapten N-(4-aminobutyl)amphetamine bound to an immunogenic carrier protein and said antibody having a higher affinity to methamphetamine than to said hapten.

* * * * *